United States Patent [19]

Van den Engh

[11] Patent Number: 5,602,349

[45] Date of Patent: Feb. 11, 1997

[54] SAMPLE INTRODUCTION SYSTEM FOR A FLOW CYTOMETER

[75] Inventor: Ger Van den Engh, Seattle, Wash.

[73] Assignee: The University of Washington, Seattle, Wash.

[21] Appl. No.: 323,348

[22] Filed: Oct. 14, 1994

[51] Int. Cl.⁶ .................................................. G01N 35/10
[52] U.S. Cl. ........................................................ 73/864.85
[58] Field of Search ........................... 73/864.85, 864.84, 73/864.86, 864.87

[56] References Cited

U.S. PATENT DOCUMENTS

| | | | |
|---|---|---|---|
| 3,299,354 | 1/1967 | Hogg | 324/71 |
| 3,661,460 | 5/1972 | Elking et al. | 356/36 |
| 3,761,941 | 9/1973 | Robertson | 346/1 |
| 3,810,010 | 5/1974 | Thom | 324/71 |
| 3,960,449 | 6/1976 | Corleton et al. | 356/340 |
| 3,963,606 | 6/1976 | Hogg | 209/3 |
| 4,014,611 | 3/1977 | Simpson et al. | 356/72 |
| 4,070,617 | 1/1978 | Kachel et al. | 324/71 |
| 4,162,282 | 7/1979 | Fulwyler et al. | 264/9 |
| 4,230,558 | 11/1980 | Fulwyler | 209/3.1 |
| 4,302,166 | 11/1981 | Fulwyler et al. | 425/6 |
| 4,317,520 | 3/1982 | Lombardo et al. | 209/3.1 |
| 4,318,480 | 3/1982 | Lombardo et al. | 209/3.1 |
| 4,318,481 | 3/1982 | Lombardo et al. | 209/3.1 |
| 4,318,482 | 3/1982 | Barry et al. | 209/3.1 |
| 4,318,483 | 3/1982 | Lombardo et al. | 209/3.1 |
| 4,325,483 | 4/1982 | Lombardo et al. | 209/3.1 |
| 4,361,400 | 11/1982 | Gray et al. | 356/23 |
| 4,395,676 | 7/1983 | Hollinger et al. | 324/71.4 |
| 4,487,320 | 11/1984 | Auer | 209/3.1 |
| 4,515,274 | 5/1985 | Hollinger | 209/3.1 |
| 4,538,733 | 9/1985 | Hoffman | 209/3.1 |
| 4,631,483 | 12/1986 | Proni et al. | 324/71.4 |
| 4,673,288 | 6/1987 | Thomas et al. | 356/72 |
| 4,691,829 | 9/1987 | Auer | 209/3.1 |
| 4,818,103 | 4/1989 | Thomas et al. | 356/72 |

(List continued on next page.)

FOREIGN PATENT DOCUMENTS

| | | | |
|---|---|---|---|
| 025296 | 3/1981 | European Pat. Off. | G01N 15/07 |
| 61-139747 | 6/1986 | Japan | G01N 15/14 |
| 61-159135 | 7/1986 | Japan | G01N 15/14 |
| 2024535 | 1/1990 | Japan | G01N 15/14 |
| 4126066 | 4/1992 | Japan | C12M 1/02 |
| 4126081 | 4/1992 | Japan | C12N 15/02 |
| 1056008 | 11/1983 | U.S.S.R. | A61B 1/00 |

OTHER PUBLICATIONS

Flow Cytometry and Cell Sorting, A. Radbruch (Ed.), "Operation of a Flow Cytometer" by Göttlinger et al., 1992, pp. 7–23.

Flow Cytometry: Instrumentation and Data Analysis, Van Dilla et al. (Eds.), "Overview of Flow Cytometry: Instrumentation and Data Analysis" by Martin Van Dilla, 1985, pp. 1–8.

Flow Cytometry: Instrumentation and Data Analysis, Van Dilla et al. (Eds.), "Flow Chambers and Sample Handling," by Pinkel et al., 1985, pp. 77–128.

Flow Cytometry and Sorting (1st Edition), Melamed, Mullaney, Mendelson, et al., John Wiley and Sons, 1979, pp. 3–9.

Primary Examiner—Thomas P. Noland
Attorney, Agent, or Firm—Luke Santangelo

[57] ABSTRACT

A sample introduction system for a flow cytometer allows easy change of sample containers such as test tubes and facilitates use in high pressure environments. The sample container includes a cap having a pressure supply chamber and a sample container attachment cavity. A sample container may be automatically positioned into the attachment cavity so as to sealably engage the end of the sample container as its outer surface. This positioning may be accomplished through some sample introduction mechanism. To facilitate cleaning, HPLC tubing and fittings may be used in a manner which facilitates removing of the entire tubing from both the nozzle container and other sample container cap to permit its replacement to avoid contamination. The sample container support may include horizontal stops which loosely limit the movement of the sample container and thus avoid further stresses upon it.

9 Claims, 3 Drawing Sheets

U.S. PATENT DOCUMENTS

| | | | |
|---|---|---|---|
| 4,845,025 | 7/1989 | Lary et al. | 435/2 |
| 4,973,196 | 8/1976 | Hogg | 324/71 |
| 4,981,580 | 1/1991 | Auer | 209/3.1 |
| 4,983,038 | 1/1991 | Ohki et al. | 356/246 |
| 5,005,981 | 4/1991 | Schulte et al. | 366/219 |
| 5,007,732 | 4/1991 | Ohki et al. | 356/73 |
| 5,079,959 | 1/1992 | Miyake et al. | 73/864.85 |
| 5,144,224 | 9/1992 | Larsen | 324/71.4 |
| 5,159,397 | 10/1992 | Kosaka et al. | 356/73 |
| 5,159,403 | 11/1992 | Kosaka | 356/243 |
| 5,167,926 | 11/1992 | Kimura et al. | 422/67 |
| 5,182,617 | 1/1993 | Yoneyama et al. | 356/440 |
| 5,199,576 | 4/1993 | Corio | 209/564 |
| 5,215,376 | 6/1993 | Schulte et al. | 366/348 |
| 5,247,339 | 9/1993 | Ogino | 356/73 |
| 5,259,593 | 11/1993 | Orme et al. | 266/78 |
| 5,260,764 | 11/1993 | Fukuda et al. | 356/73 |
| 5,359,907 | 11/1994 | Baker et al. | 73/865.5 |
| 5,370,842 | 12/1994 | Miyazaki et al. | 422/82.06 |
| 5,412,466 | 5/1995 | Ogino | 356/246 |

SAMPLE INTRODUCTION SYSTEM FOR A FLOW CYTOMETER

The U.S. Government has a paid-up license in this invention and the fight in limited circumstances to require the patent owner to license others on reasonable terms as provided for by the terms of a contract number DE-FG06-93ER-61662 awarded by the Department of Energy.

BACKGROUND OF THE INVENTION

This invention relates to flow cytometers which are designed for repetitive processing of substances. Specifically, the invention relates to systems which repetitively introduce samples without contamination for high speed processing. It is particularly suited to sorting and analysis applications in both the clinical and research fields.

Flow cytometers have been in clinical and research use for many years. Basically, the systems act to position small amounts of a substance within a sheath fluid. This sheath fluid may either form droplets or may exist within a transparent channel for optical analysis. Through hydrodynamic focusing and laminar flow, the substance is split into individual cells and the like and is surrounded by a sheath fluid. Since individual cells and the like are often processed, the speed at which substance material can be processed is somewhat limited.

In many applications the substance involves a liquid which is frequently changed. This may include processing a sample from one patient to another. These changes further limit the speed at which processing may occur. Further samples tested can also involve biologically active materials such as viruses and the like. This can intensify the need to thoroughly clean and decontaminate the system when changing samples.

In use, it is typical to receive sample substances as liquids contained within test tubes. These test tubes are attached or inserted into a flow cytometer system which pressurizes the test tube and thus forces the substance through tubing and into a nozzle container of the flow cytometer. For convenience, the test tubes are often attached by inserting a stopper into the test tube top. These stoppers often had two tubes positioned through them: a tube for supplying pressure to the test tube and a tube for allowing the substance to flow out of the test tube. As indicated in U.S. Pat. No. 5,182,617, a variety of designs have been proposed to facilitate more rapid processing. These designs have, however, not totally met the needs of those involved in the actual processing of samples.

One of the problems faced has been the stresses placed upon the test tube or other container as it is pressurized for use. Because of the relationship between the speed of processing and the pressure applied to the sample container, this problem is intensified as higher processing speeds are pursued. While naturally other containers other than a test tube could be used, the time required to transfer substance to some more appropriate container and the additional decontamination potentially required has made such solutions generally undesirable. In some applications, those involved have simply utilized the conventional components closer to their inherent limitations and may have even limited the performance of the flow cytometer to accommodate such limitations. Obviously, such an approach, although practical, is undesirable.

Yet another problem faced by those skilled in the art is the fact that the proper combination of features and performance for practical use of a flow cytometer for repetitive sampling of substances has not yet been achieved. Apart from the actual analysis capability of the flow cytometer, it is necessary to provide a system which those involved in the actual usage of the system find convenient. For some applications, this involves providing a system which can be easily cleaned or decontaminated between sample runs. In others an easily manipulatable and inexpensive system may be desired. The present invention combines features to achieve a practicably implementable system which meets each of these needs (and other needs more appropriately).

As mentioned, when biologically active materials are used, the problem of contamination is of greater concern. Not only has this mandated more thorough cleaning of the system between uses, but it also has made the problem of aerosols more acute. As pressure is applied to the sample container, this pressure—and the air flows associated with it—can result in the creation of aerosols which may contain a biologically active substance. Naturally, this must be avoided. Through potentially independent features, the present invention acts to minimize the creation of the aerosols in the first place.

As explained, a number of the foregoing problems have long been recognized by those having ordinary skill in the art. Solutions, however, have not been achieved in a practical and efficient manner even though the implementing arts have long been available. To some extent, this may be due to the fact that those having ordinary skill in the art may not have fully appreciated the nature of the problems or may have simply failed to consider designs which could be practically adapted to traditional components. Indeed, the directions taken by those skilled in the art have to some degree been directed away from the directions taken in the present invention. Until the present invention a system which simultaneously met the needs for high speed processing for changing samples, for cleaning the system, and for avoiding contamination was not practically available for many applications.

SUMMARY OF THE INVENTION

The present invention involves improvements which may be implemented in conventional systems in a variety of ways. As to one feature, the invention discloses a system which acts to seal the flow cytometer around the exterior of the sample container to avoid and minimizes the effects of the stresses placed upon such a container when it is pressurized. This system is provided through an operating mechanism which both facilitates use and may be easily disassembled and cleaned. The operating mechanism is designed to accommodate high pressure fittings in a manner which allows for the complete removal, disposal, and/or replacement of tubing components and the like to further minimize contamination concerns. Each of these are designed to facilitate the use of higher pressures as may be associated with high speed processing. In addition, the sample container cap (which is designed to seal around the exterior of a test tube and the like) is designed so as to apply pressure in a manner which minimizes the possibility of the creation of aerosols from the substance used by being angled away from the substance.

Accordingly, it is an object of the invention to facilitate the use of traditional components in more demanding applications. In keeping with this object, a goal is to provide designs which reduce the stresses on sample containers such as test tubes and the like. It is also an object to provide for a system which is capable of use at higher pressures and higher processing speeds. The design is configured so as to minimizes the limitations placed upon systems as a result of the structure of the components utilized. The design also has as a goal accommodating the unavoidable movement of the sample container during the processing procedure.

Another object of the invention is to reduce—and eliminate where possible—the possibility of aerosols being created as a result of the sample introduction facet of the processing procedure. Thus a goal is to allow the use of a pressure feed system which does not act to create aerosols when in use. A goal is also to direct the pressure away from the substance so that gas flows tend not to exist at the surface of the substance.

A broadly stated object of the invention is to provide a system which is easy for the operator to use. In keeping with this object, a goal is to allow for one-step operation where possible when attaching the sample container. Another goal is to allow for easy cleaning and decontamination of the entire system. Thus a goal is to provide for a system which may be easily disassembled and which includes replaceable and disposable components.

Naturally, further objects of the invention are disclosed throughout other areas of the specification and claims.

DETAILED DESCRIPTION OF THE PREFERRED EMBODIMENT

Figure 1:
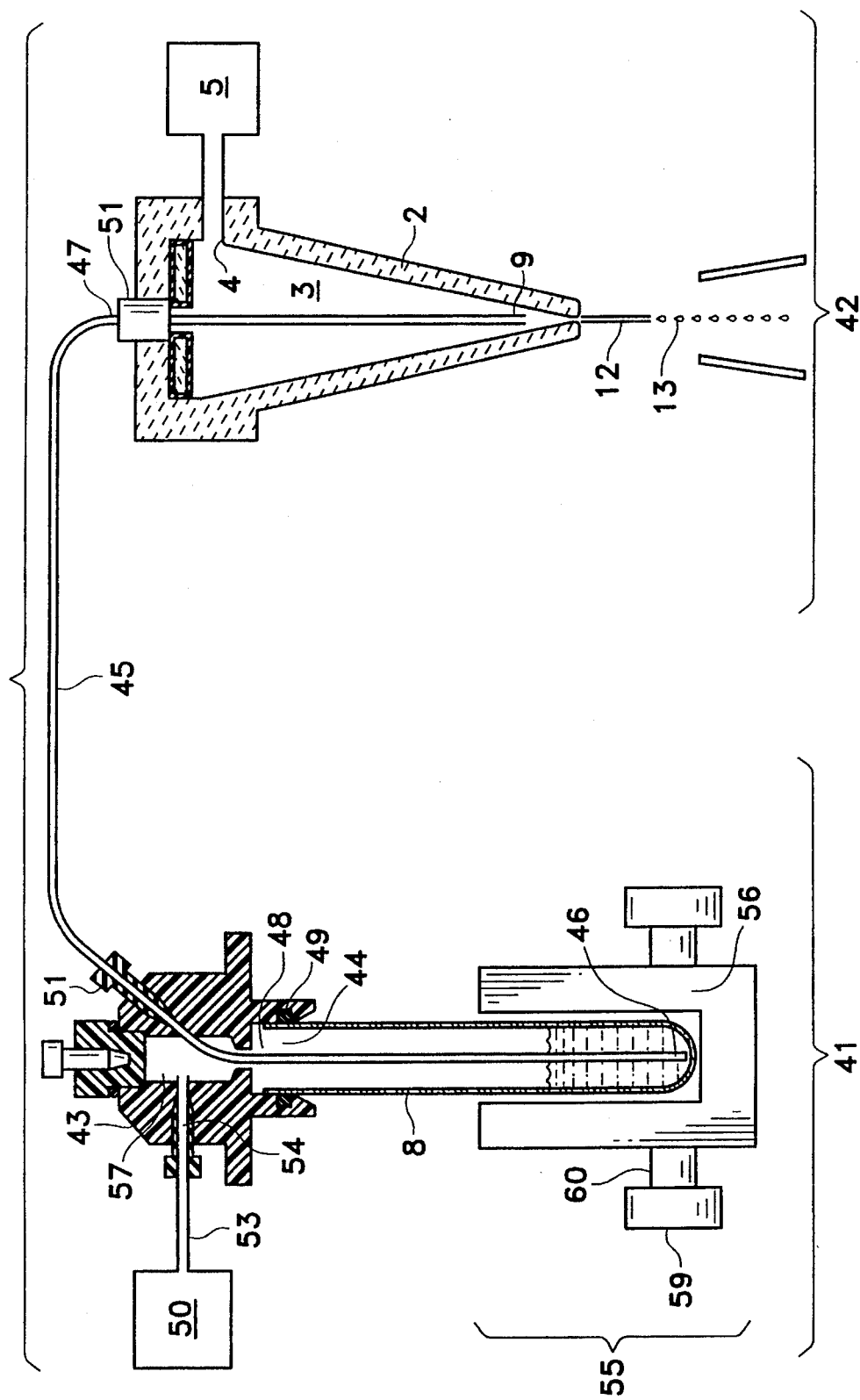
FIG. 1 is a schematic cross-sectional view of a sample introduction system according to the present invention as applied to a droplet flow cytometer.

As can be seen from the drawings and in keeping with the objects of the invention, the basic concepts of the present invention are easily implemented. FIG. 1 shows one design through which this is possible. As it shows, the flow cytometer (1) incudes a sample introduction system (41) and a nozzle system (42). Generally, sample introduction system (41) acts to provide the appropriate flow of some sample material to nozzle system (42) so as to permit processing. As is well understood by those having ordinary skill in the art, this processing typically involves the introduction of a sheath fluid through sheath fluid port (4) into nozzle volume (3) from some sheath reservoir (5). This sheath fluid has introduced to it the substance through substance introduction port (9). Together, the substance and the sheath fluid may then exit nozzle container (2) in jet (12) so as to form droplets (13) for processing. This processing may include sorting through the differential application of charge to the various droplets (13) as those skilled in the art readily understand. Additionally, it should be understood that although FIG. 1 shows sample introduction system (41) as attached to nozzle system (42) configured as a droplet flow cytometer, naturally, sample introduction (41) can be applied to other flow cytometer designs as well. This would include channel type flow cytometers as those skilled in the art would readily understand. Such systems may act to direct flow within a sealed channel or may cause a continuous jet to flow without forming into regular droplets As shown in FIG. 1, the particular configuration of sample introduction system (41) has a number of features. First, it can be seen that sample container (8) includes the test tube configuration shown. Such a container may be made of plastic, glass, or any other material. Sample container (8) is attached to substance supply tube (45) through use of a sample container cap (43) which is situated over top end (44) of sample container (8).

In order to introduce the substance, sample container cap (43) has attached to it, substance supply tube (45). [It may also have a separate port for hypodermic insertion of a substance as shown in FIG. 1, however, this element is not an aspect of the present invention.] As shown, substance supply tube (45) may be positioned on the vertical axis of sample container cap (43) so that second end (46) of substance supply tube (45) is positioned into sample container (8). In this fashion when pressure is applied to sample container (8), the substance is forced through second end (46) of substance supply tube (45) so as to pass into nozzle volume (3) and be emitted from substance introduction port (9). This substance introduction port (9) may actually be the end of a stainless steel tube which is attached to first end (47) of substance supply tube (45).

As shown, sample container cap (43) is configured to have sample container (8) easily attached to it. To facilitate this, sample container cap (43) has an inner surface which forms sample container attachment cavity (48). This attachment cavity (48) may be positioned about top end (44) of sample container (8) so as to sealably engage the outer surface of sample container (8). This sealing effectively establishes substance supply tube (45) sealed to sample container (8). In the design shown, this may be accomplished through the use of O-ring (49) which acts as an external seal. In this fashion, when pressure is applied to sample container (8) it does not urge sample container (8) away from the seal as in conventional designs but rather urges it in a tighter fashion against the external seal. Thus by providing O-ring (49) positioned on the inner surface of sample container cap (43) and against the outer surface of sample container (8), the pressure applied by pressure source (50) actually can enhance the seal. Further, in sealing substance supply tube (45) to sample container (8), sample container cap (43) has substance supply tube (45) attached to it through removable tubing seal (51). Through this design, the entire length of substance supply tube (45) may be removed, replaced, or cleaned.

Figure 2:
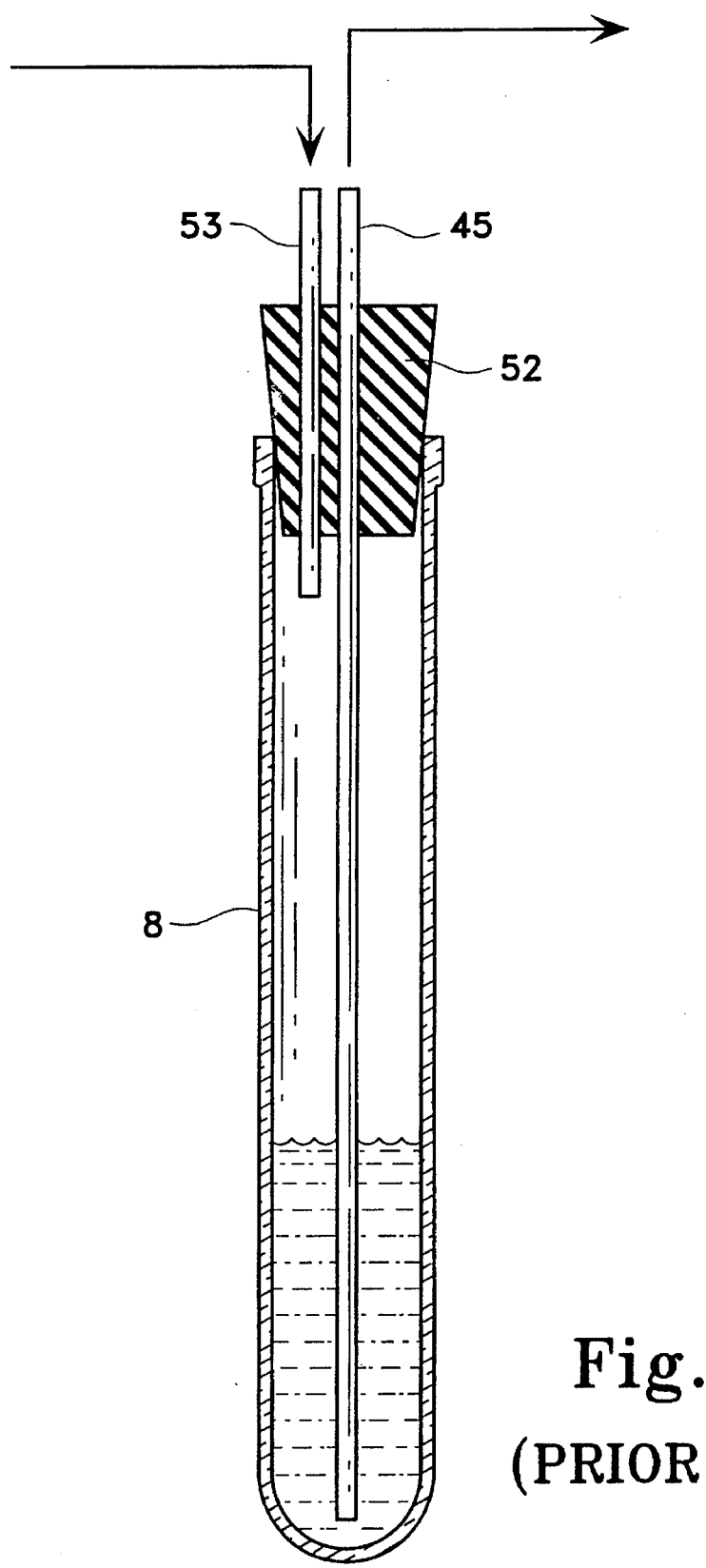
FIG. 2 is a diagram of a conventional test tube introduction design.

With this understanding, it can be seen how the present design differs in one regard from the prior art. Referring to FIG. 2, it can be seen how the prior art traditionally involves stopper (52) through which substance supply tube (45) passes. Upon applying pressure through pressure tube (53), sample container (8) is urged away from stopper (52). In sharp contrast, the present design accomplishes exactly the opposite, namely, upon applying pressure through angled pressure source (54) (the angled aspect of this element is discussed later) sample container (8) is urged against O-ring seal (49) and thus the seal is actually enhanced by the pressure. Additionally, the stresses on conventional designs are caused by both the pressure and stopper (52) in a manner which compounds. Again, in sharp contrast, the stresses on sample container (8) of the present invention oppose each other and thus minimize the effect upon it.

Referring again to FIG. 1, it can be seen how even when in use the design is less delicate. This is in part through the design of sample container support (55). As shown, sample container support (55) is designed to receive sample container (8) and support it vertically. Thus, sample container support (55) engages the bottom of sample container (8) and supports it along the vertical axis by being situated below sample container cap (43). Although not a requirement, it may be desirable for some applications to design sample container support (55) so as to include horizontal stops (56) which are generally detached from sample container (8) when it is inserted. Horizontal stops (56) can thus allow some limited movement in the horizontal plane and thus act to loosely limit sample container (8). This can be advantageous since sample container (8) may be a delicate component such as a glass test tube. In this fashion, whether sample container cap (43) is operated manually, remotely, or through some mechanism, unnecessary stresses on sample container (8) can be avoided to an even greater degree.

As mentioned earlier, two of the goals of the invention include providing a design which can be easily cleaned and decontaminated as well as a design which facilitates the use of higher pressures for faster processing. Each of these are accommodated through the designs shown. First, through the selection of tubing and fittings such as those used in high pressure liquid chromatography (HPLC) applications, the use of high pressures is possible. Second, these designs (as well as any others selected) are accommodated in a manner so as to allow substance supply tube (45) to be removable from the components. Thus, sample container cap (43) is designed to allow attachment and detachment of substance supply tube (45) at removable tubing seal (51). Similarly, nozzle container (2) is also designed to accommodate the same type of removable tube seal (51). When changing substances, it is now possible to remove all of substance supply tube (45) and replace it. This greatly facilitates decontamination as it is very difficult to thoroughly clean substance supply tube (45) through back flushing and the like. Additionally, the design of substance supply cap (43) permits tubing to be attached at removable tube seal (51) while simultaneously allowing substance supply tubing (45) to pass through sample container cap (43) and down into sample container (8). Through these features not only can substance supply tubing (45) be replaced but also sample container cap (43) may be removed from the flow cytometer for decontamination as well as nozzle container (2) and substance introduction port (9). Each of these components may then be chemically and/or heat treated for easier decontamination.

Referring to the conventional design shown in FIG. 2, it can be understood how the introduction of pressure through pressure tube (53) can cause the creation of aerosols within sample container (8). While this problem seems to have a very simple solution, in fact, those skilled in the art had not, prior to the present invention, practically achieved such solutions. Instead, the use of stopper (52) lent itself to the inclusion of pressure tube (53) in such a manner so as to allow gas flows from this pressure to impinge directly upon the substance contained within sample container (8). To the contrary, the design shown in FIG. 1 avoids this aspect. As shown, sample container cap (43) has included on its inner surface angled pressure source (54) which directs air into pressure supply chamber (57). In a basic form, the pressure is applied at an angle to the vertical axis of sample introduction system (41) (and likewise to sample container cap (43)) so as to avoid any direct gas flow onto the substance contained within sample container (8). As shown, the angle at which the gas flows supplying the pressure are emitted may be about 90 degrees to that of the vertical axis of sample container cap (43). Further, to additionally minimize the gas flows experienced at the surface of the substance within sample container (8), pressure supply chamber (57) may be baffled or otherwise designed. As shown, it is simply enlarged so as to avoid having a narrow stream of gas move toward the substance.

Figure 3:
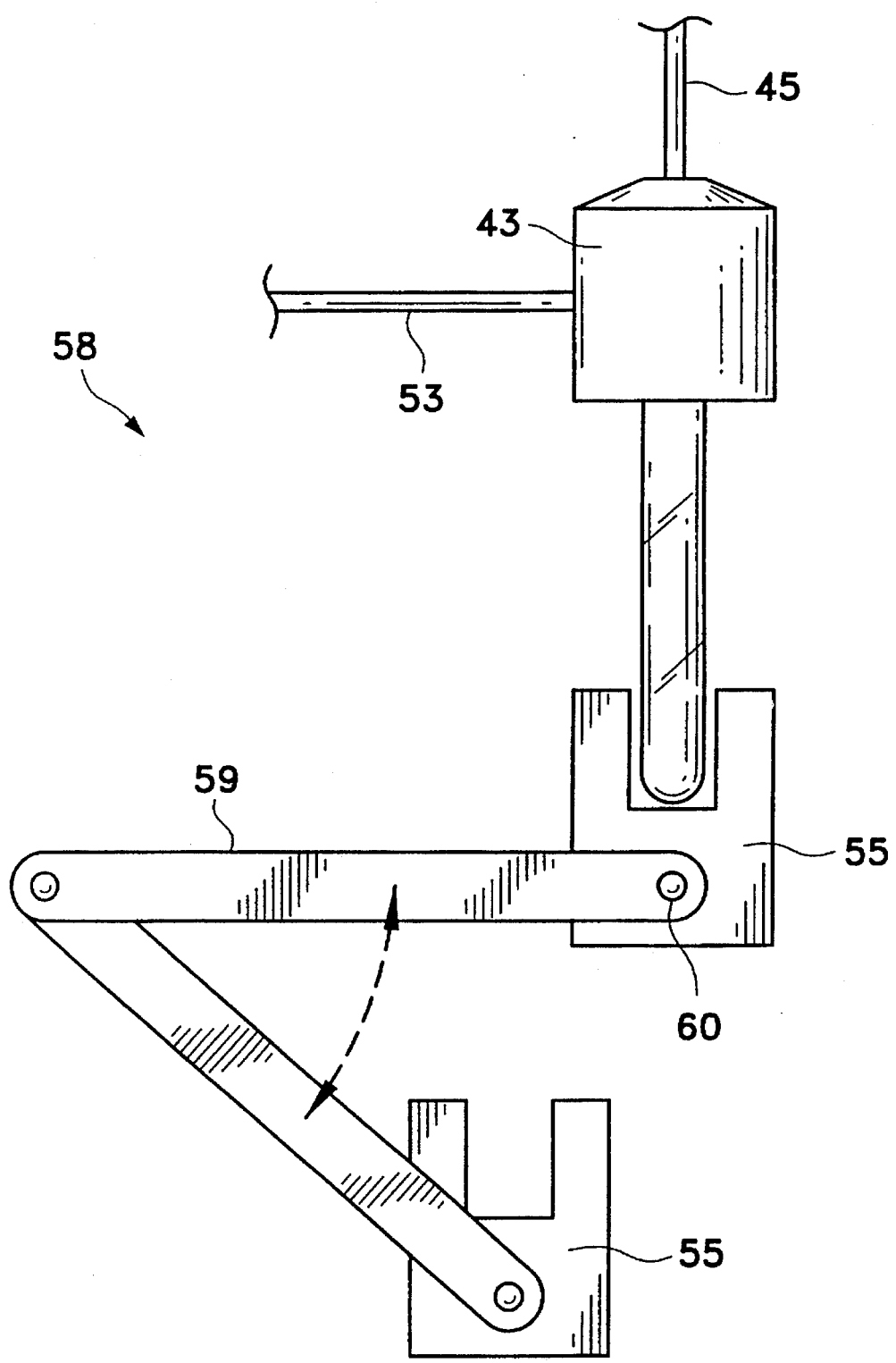
FIG. 3 is a side view of the embodiment of FIG. 1 showing the cap raising mechanism operation.

Finally, referring to FIG. 3, sample introduction mechanism (58) may be easily understood. As shown sample introduction mechanism (58) may include one or more arms (59) which attach to the outer surface of sample container support (55) at one or more attachment points (60). By operating sample introduction mechanism (58) sample container cap (43) may be engaged by the top of sample container (8) to allow easy sample changing. Naturally this mechanism may be designed in a host of different fashions, may be automated, or may be manually operated. Such designs would include configurations which would tend to automatically attach and hold sample container during the removal process as well as designs which might purposely move sample container support (55) parallel to its vertical axis initially so as to avoid any additional stresses upon sample container (8).

The foregoing discussion and the claims which follow describe the preferred embodiment of the present invention. Particularly with respect to the claims it should be understood that changes may be made without departing from the essence of this patented invention. It is intended that such changes are permissible to accommodate varying applications and will still fall within the scope of this patent as it is simply not practical to describe and claim all possible revisions to the design. To the extent such revisions utilize the essence of the invention each would naturally fall within the breadth of protection encompassed by this patent.

I claim:

1. A method of introducing a sample for flow cytometer processing comprising the steps of:
   a. establishing a nozzle volume;
   b. attaching a substance supply tube to said nozzle volume;
   c. attaching a sample container having an outer surface to said substance supply tube, said sample container serving as a reservoir for a substance to be supplied via the supply tube to the nozzle volume;
   d. sealing said sample container to said substance supply tube by a seal which engages said sample container about said outer surface;
   e. introducing a flow of sheath fluid into said nozzle volume;
   f. applying a pressure to said sample container; and
   g. allowing said substance to flow from said sample container to said sheath fluid in said nozzle volume.

2. A method of introducing a sample for flow cytometer processing as described in claim 1 wherein said sample container is attached to a sample container cap and wherein said step of attaching a sample container comprises the step of operating a sample introduction mechanism.

3. A method of introducing a sample for flow cytometer processing as described in claim 2 wherein said step of attaching said sample container further comprises the steps of:
   a. supporting said sample container vertically; while
   b. loosely limiting said sample container so as to permit some movement of said sample container horizontally.

4. A method of introducing a sample for flow cytometer processing as described in claim 1 wherein said sample container has an axis and wherein said step of applying a pressure to said sample container comprises the step of applying said pressure through an element oriented at an angle to said axis.

5. A method of introducing a sample for flow cytometer processing as described in claim 4 wherein the angle is about 90 degrees.

6. A method of introducing a sample for flow cytometer processing as described in claim 4 wherein said axis is vertical.

7. A method of introducing a sample for flow cytometer processing comprising the steps of:
   a. establishing a nozzle volume;
   b. attaching a substance supply tube to said nozzle volume;
   c. attaching a sample container having an axis to said substance supply tube, said sample container serving as a reservoir for a substance to be supplied via the supply tube to the nozzle volume;
   d. introducing a flow of sheath fluid into said nozzle volume;
   e. applying a pressure to said sample container through an element oriented at an angle to said axis; and
   f. allowing said substance to flow from said sample container to said sheath fluid in said nozzle volume.

8. A method of introducing a sample for flow cytometer processing as described in claim 7 wherein the angle is about 90 degrees.

9. A method of introducing a sample for flow cytometer processing as described in claim 7 wherein said axis is vertical.

* * * * *